(12) United States Patent
Hahn et al.

(10) Patent No.: US 7,404,883 B2
(45) Date of Patent: Jul. 29, 2008

(54) INSULATION BUSHING ASSEMBLY FOR AN EXHAUST GAS SENSOR

(75) Inventors: Norman Hahn, Anderson, SC (US); Grady Prewitt, Anderson, SC (US); Craig Magera, Simpsonville, SC (US)

(73) Assignee: Robert Bosch GmbH, Stuttgart (DE)

( * ) Notice: Subject to any disclaimer, the term of this patent is extended or adjusted under 35 U.S.C. 154(b) by 843 days.

(21) Appl. No.: 10/822,417

(22) Filed: Apr. 12, 2004

(65) Prior Publication Data

US 2005/0224347 A1    Oct. 13, 2005

(51) Int. Cl.
   *G01N 27/407*    (2006.01)
(52) U.S. Cl. .................. 204/428; 204/424; 439/260
(58) Field of Classification Search .......... 204/424, 204/428, 427; 439/260
   See application file for complete search history.

(56) References Cited

U.S. PATENT DOCUMENTS

| | | | |
|---|---|---|---|
| 2,879,583 A | 3/1959 | Booth et al. |
| 3,007,810 A | 11/1961 | Hobrock |
| 3,574,033 A | 4/1971 | Kolkman et al. |
| 3,916,071 A | 10/1975 | Kinnebrew et al. |
| 4,001,758 A | 1/1977 | Esper et al. |
| 4,107,018 A | 8/1978 | Bode et al. |
| 4,127,424 A | 11/1978 | Ullery, Jr. |
| 4,130,797 A | 12/1978 | Hattori et al. |
| 4,133,910 A | 1/1979 | Ruwe et al. |
| 4,155,827 A | 5/1979 | Maurer et al. |
| 4,212,720 A | 7/1980 | Maurer et al. |
| 4,264,647 A | 4/1981 | Trevorrow |
| 4,296,148 A | 10/1981 | Friese |
| 4,305,803 A | 12/1981 | Beyer et al. |
| 4,310,401 A | 1/1982 | Stahl |
| 4,338,362 A | 7/1982 | Turcotte |
| 4,339,320 A | 7/1982 | Friese et al. |
| 4,413,502 A | 11/1983 | Ohta et al. |
| 4,419,212 A | 12/1983 | Dietz et al. |
| 4,490,411 A | 12/1984 | Feder |
| 4,504,522 A | 3/1985 | Kaiser et al. |
| 4,540,479 A | 9/1985 | Sakurai et al. |
| 4,556,475 A | 12/1985 | Bayha et al. |

(Continued)

FOREIGN PATENT DOCUMENTS

DE    10225896 A1    8/2004

(Continued)

OTHER PUBLICATIONS

Figs. B-R illustrate an admitted prior art Bosch exhaust gas sensor and various components thereof (see attached Description of Figures), date unknown.

*Primary Examiner*—Kaj K Olsen
(74) *Attorney, Agent, or Firm*—Michael Best & Friedrich LLP (57) ABSTRACT

An insulation bushing assembly for use with an exhaust gas sensor. The insulation bushing assembly includes an insulation bushing having a passageway defining a surface, and a contact plate assembly having a contact plate coupled with the insulation bushing. A resilient member extends from the contact plate and into the passageway. The resilient member is engageable with the surface of the passageway such that the member is deflected by the surface from an undeflected position with respect to the contact plate to a deflected position with respect to the contact plate to retain the contact plate assembly in engagement with the bushing.

31 Claims, 12 Drawing Sheets

U.S. PATENT DOCUMENTS

| | | | |
|---|---|---|---|
| 4,595,614 | A | 6/1986 | Nunlist |
| 4,597,850 | A | 7/1986 | Takahasi et al. |
| 4,693,538 | A | 9/1987 | Matsuo |
| 4,701,348 | A | 10/1987 | Neville |
| 4,773,376 | A | 9/1988 | Uchikawa et al. |
| 4,806,455 | A | 2/1989 | LaBianca |
| 4,930,700 | A | 6/1990 | McKown |
| 4,943,330 | A | 7/1990 | Iino et al. |
| 5,017,340 | A | 5/1991 | Pribat et al. |
| 5,032,568 | A | 7/1991 | Lau et al. |
| 5,096,734 | A | 3/1992 | Nikulainen et al. |
| 5,104,042 | A | 4/1992 | McKown |
| 5,116,263 | A | 5/1992 | Bennett et al. |
| 5,139,639 | A | 8/1992 | Holleboom |
| 5,169,513 | A | 12/1992 | Mase et al. |
| 5,190,482 | A | 3/1993 | VanDerStuyf et al. |
| 5,316,503 | A | 5/1994 | Thompson et al. |
| 5,328,728 | A | 7/1994 | Swirbel et al. |
| 5,329,806 | A | 7/1994 | McClanahan et al. |
| 5,346,605 | A | 9/1994 | Wolcott et al. |
| 5,372,775 | A | 12/1994 | Hayashi et al. |
| 5,423,972 | A | 6/1995 | Mann et al. |
| 5,522,979 | A | 6/1996 | Tatumoto et al. |
| 5,546,787 | A | 8/1996 | Hafele et al. |
| 5,573,650 | A | 11/1996 | Fukaya et al. |
| 5,626,499 | A | 5/1997 | Yagi et al. |
| 5,670,032 | A | 9/1997 | Friese et al. |
| 5,711,863 | A | 1/1998 | Henkelmann et al. |
| 5,736,095 | A | 4/1998 | Shimada et al. |
| 5,739,414 | A | 4/1998 | Paulus et al. |
| 5,780,100 | A | 7/1998 | McCabe et al. |
| 5,804,050 | A | 9/1998 | Hayakawa et al. |
| 5,817,920 | A | 10/1998 | Kuisell et al. |
| 5,846,391 | A | 12/1998 | Friese et al. |
| 5,886,248 | A | 3/1999 | Paulus et al. |
| 5,900,129 | A | 5/1999 | Tsuji et al. |
| 5,922,938 | A | 7/1999 | Hafele |
| 5,935,399 | A | 8/1999 | Tanaka et al. |
| 5,942,092 | A | 8/1999 | Weyl et al. |
| 5,948,225 | A | 9/1999 | Katafuchi et al. |
| 5,955,656 | A | 9/1999 | Graser et al. |
| 6,063,249 | A | 5/2000 | Duce et al. |
| 6,068,524 | A | 5/2000 | Koumatsu |
| 6,068,746 | A | 5/2000 | Kojima et al. |
| 6,074,694 | A | 6/2000 | Friese et al. |
| 6,082,175 | A | 7/2000 | Yoshikawa et al. |
| 6,096,372 | A | 8/2000 | Nomura et al. |
| 6,164,120 | A | 12/2000 | Friese et al. |
| 6,206,377 | B1 | 3/2001 | Weyl |
| 6,246,000 | B1 | 6/2001 | Wehrmann et al. |
| 6,266,997 | B1 | 7/2001 | Nelson |
| 6,273,432 | B1 | 8/2001 | Weyl et al. |
| 6,319,376 | B1 | 11/2001 | Graser et al. |
| 6,342,141 | B1 | 1/2002 | Nelson |
| 6,408,680 | B2 | 6/2002 | Friese et al. |
| 6,486,605 | B1 | 11/2002 | Beunas et al. |
| 6,527,573 | B2 * | 3/2003 | Maga et al. ............... 439/260 |
| 6,589,612 | B1 | 7/2003 | Cintra et al. |
| 2003/0074950 | A1 | 4/2003 | Yamada et al. |

FOREIGN PATENT DOCUMENTS

| | | |
|---|---|---|
| EP | 1391724 A1 | 2/2004 |
| WO | WO 01/34951 A2 | 5/2001 |

* cited by examiner

INSULATION BUSHING ASSEMBLY FOR AN EXHAUST GAS SENSOR

FIELD OF THE INVENTION

This invention relates generally to exhaust gas sensors, and more particularly to insulation bushing assemblies for exhaust gas sensors.

BACKGROUND OF THE INVENTION

Exhaust gas sensors are well known in the automotive industry for sensing the oxygen, carbon monoxide, or hydrocarbon content of the exhaust stream generated by internal combustion engines. Stoichiometric or "Nemst"-type oxygen sensors (a widely used type of exhaust gas sensor) measure the difference between the partial pressure of oxygen found in the exhaust gas and oxygen found in the atmosphere. By determining the amount of oxygen in the exhaust gas, the oxygen sensor enables the engine control unit ("ECU") to adjust the air/fuel mixture and achieve optimal engine performance. Other types of exhaust gas sensors that operate based on different principles are also known and widely used in the automotive industry.

SUMMARY OF THE INVENTION

The present invention provides an improved insulation bushing assembly for an exhaust gas sensor and an improved method of assembling an exhaust gas sensor.

More particularly, the present invention provides, in one aspect, an insulation bushing assembly for use with an exhaust gas sensor. The insulation bushing assembly includes an insulation bushing including a passageway defining a surface. The insulation bushing assembly also includes a contact plate assembly having a contact plate coupled with the insulation bushing and a resilient member extending from the contact plate for insertion into the passageway. The resilient member is engageable with the surface of the passageway during insertion such that the member is deflected by the surface from an undeflected position with respect to the contact plate to a deflected position with respect to the contact plate.

The present invention provides, in another aspect, an exhaust gas sensor including a sensor housing, a sensor element at least partially enclosed within the housing, and an insulation bushing at least partially supported within the housing. The insulation bushing includes a passageway defining a surface. The exhaust gas sensor also includes a contact plate assembly having a contact plate coupled with the insulation bushing and the sensor element. A resilient member extends from the contact plate for insertion into the passageway. The resilient member is engageable with the surface of the passageway during insertion such that the member is deflected by the surface from an undeflected position with respect to the contact plate to a deflected position with respect to the contact plate.

The present invention provides, in yet another aspect, a method of assembling an exhaust gas sensor. The method includes providing an insulation bushing including a passageway defining a surface, providing a contact plate assembly including a contact plate and a resilient member extending from the contact plate, inserting the resilient member into the passageway, engaging the resilient member with the surface, and deflecting the member from an undeflected position with respect to the contact plate to a deflected position with respect to the contact plate.

Other features and aspects of the present invention will become apparent to those skilled in the art upon review of the following detailed description, claims and drawings.

BRIEF DESCRIPTION OF THE DRAWINGS

In the drawings, wherein like reference numerals indicate like parts:

FIG. 4a is a partially assembled cross-sectional view of the insulation bushing assembly of FIG. 3 taken through section line 4a-4a.

FIG. 5a is an assembled cross-sectional view of the insulation bushing assembly of FIG. 3 taken through section line 5a-5a.

FIG. 6b is a perspective view of another construction of the insulation bushing of FIG. 6a.

FIG. 6c is a perspective view of yet another construction of the insulation bushing of FIG. 6a.

FIG. 9a is a partially assembled cross-sectional view of the insulation bushing assembly of FIG. 8 taken through section line 9a-9a.

FIG. 10a is an assembled cross-sectional view of the insulation bushing assembly of FIG. 8 taken through section line 10a-10a.

FIG. 13a is a partially assembled cross-sectional view of the insulation bushing assembly of FIG. 12 taken through section line 13a-13a.

FIG. 14a is an assembled cross-sectional view of the insulation bushing assembly of FIG. 12 taken through section line 14a-14a.

Before any features of the invention are explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein is for the purpose of description and should not be regarded as limiting. The use of "including", "having", and "comprising" and variations thereof herein is meant to encompass the items listed thereafter and equivalents thereof as well as additional items. The use of letters to identify elements of a method or process is simply for identification and is not meant to indicate that the elements should be performed in a particular order.

DETAILED DESCRIPTION

Figure 1:
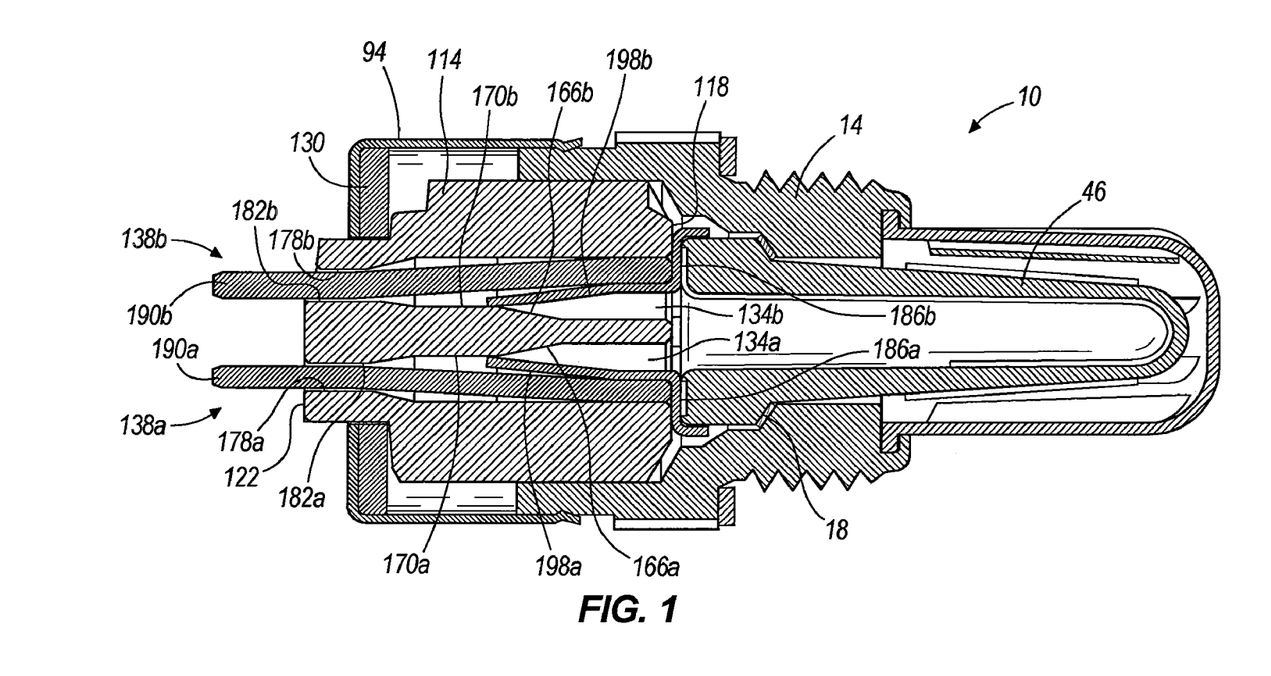
FIG. 1 is a cross-sectional view of an exhaust gas sensor of the present invention.
Figure 2:
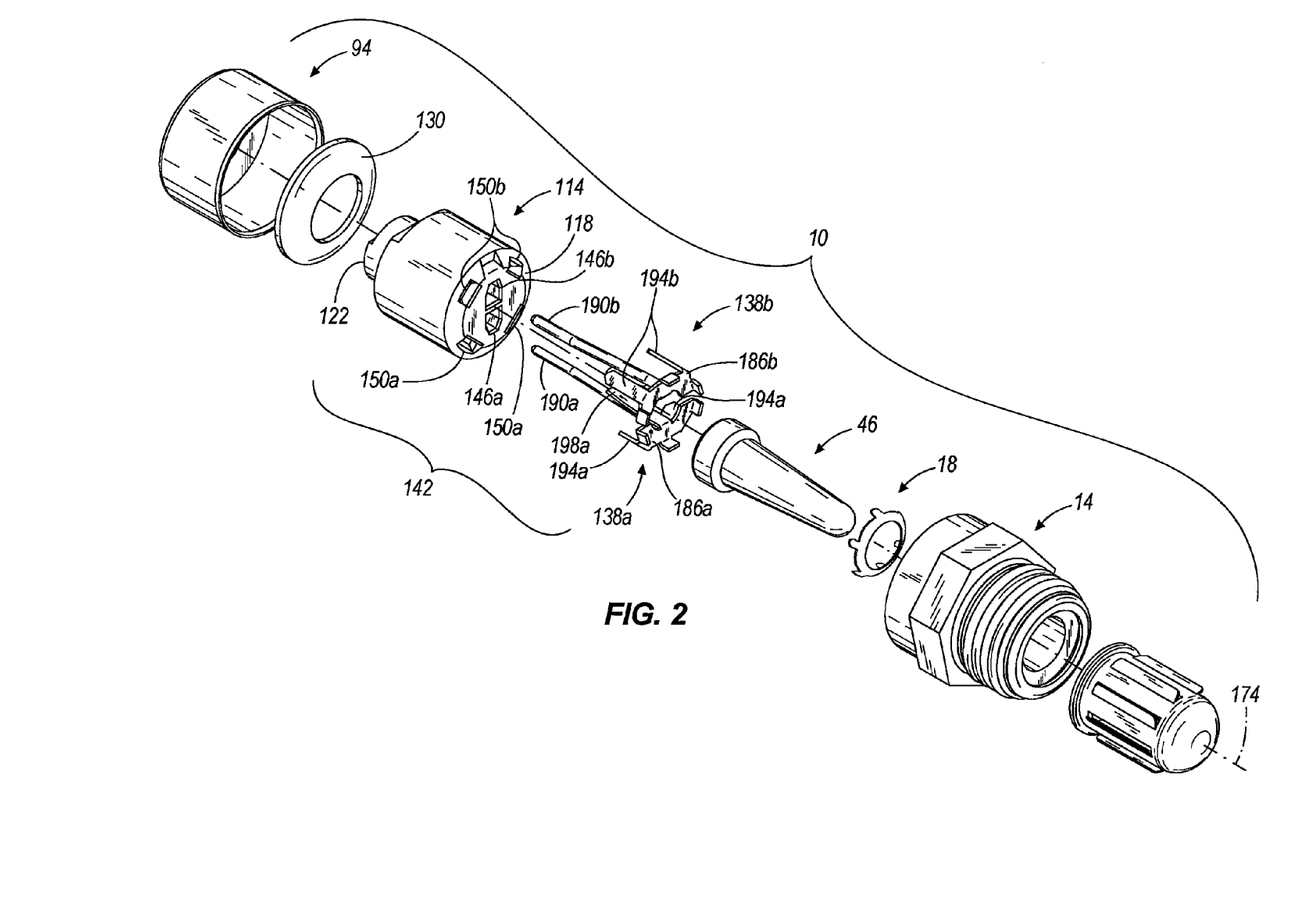
FIG. 2 is an exploded perspective view of the components of the sensor of FIG. 1.

FIG. 1 illustrates an exhaust gas sensor 10 of the present invention. The illustrated sensor 10 is an unheated, two-wire sensor 10. However, those skilled in the art will understand that the sensor 10 could be modified to be a single-wire sensor.

The sensor 10 includes a generally cylindrical metallic housing 14 threadably engaged with a threaded aperture of an exhaust pipe (not shown) or other component of an internal combustion engine (also not shown) used for automotive applications or non-automotive applications, such as motorcycles, snowmobiles, ATV's, lawnmowers, and the like.

The housing 14 receives and supports a sensor element 46 including an outer or exhaust electrode communicating with the exhaust gas stream, and an inner or reference electrode communicating with reference air, as understood by those skilled in the art. A seal ring 18 is positioned between the sensor element 46 and the housing 14 to seal the sensor element 46 to the housing 14. Reference is made to U.S. patent application Ser. No. 10/610,479 filed on Jun. 30, 2003, now U.S. Pat. No. 6,843,105, the entire contents of which are incorporated herein by reference, for discussion of additional features of the housing 14 and the sensor element 46 not described herein.

The sensor 10 further includes a sleeve 94 connected to the housing 14. An insulation bushing 114 is disposed within the sleeve 94 and includes a first end 118 received in the housing 14 and a second end 122 at least partially extending out of the sleeve 94. A disk spring 130 is disposed between the sleeve 94 and the bushing 114 to bias the bushing 114 toward the housing 14. In the illustrated construction, the bushing 114 is made of ceramic materials known as soapstone steatite or crypto-crystalline talc, and in some instances, can be made from materials having lower thermal conductivity and higher compressive strength, such as DOTHERM DT600M available from Industria Engineering Products in Uxbridge, United Kingdom.

With continued reference to FIG. 1, the bushing 114 includes two internal passageways 134a, 134b extending therethrough. The passageways 134a, 134b receive respective "signal" and "ground" contact plate assemblies 138a, 138b that electrically connect the reference electrode and the exhaust electrode to respective wire leads extending from the sensor 10 for electrical connection to the ECU. The wire leads, in addition to other components (e.g., seals, grommets, and the like) that may be used with the sensor 10, are shown in the previously-referenced U.S. Pat. No. 6,843,105.

The contact plate assemblies 138a, 138b are made from an electrically conducive material, such as metal. The bushing 114 thereby electrically isolates the contact plate assemblies 138a, 138b from the housing 14 and the sleeve 94. Additionally, the internal passageways 134a, 134b electrically isolate the signal contact plate assembly 138a from the ground contact plate assembly 138b.

Figure 3:
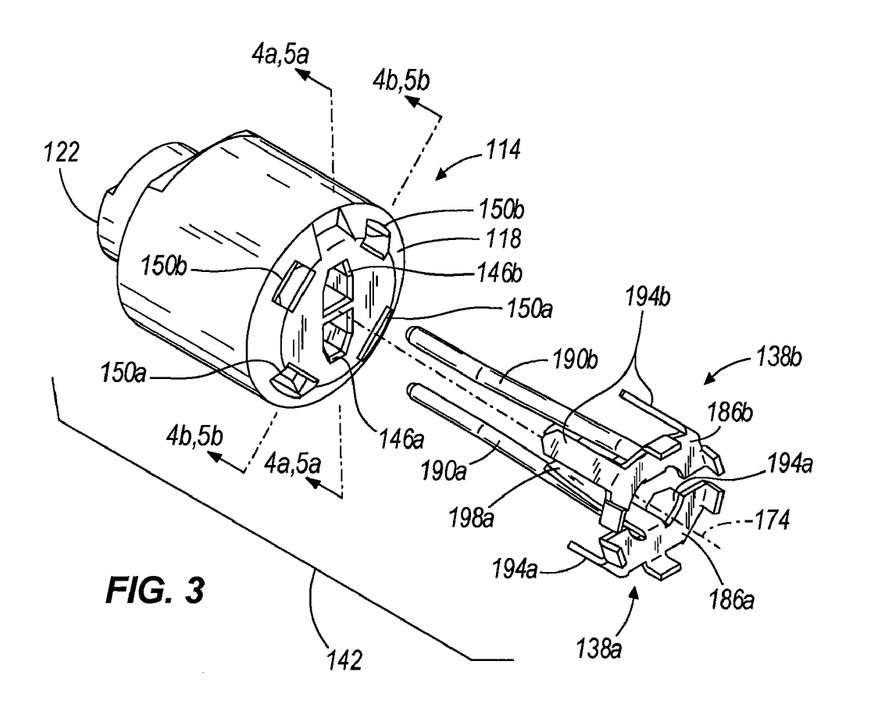
FIG. 3 is an enlarged, exploded, perspective view of an insulation bushing assembly from the sensor of FIG. 1.
Figure 6A:
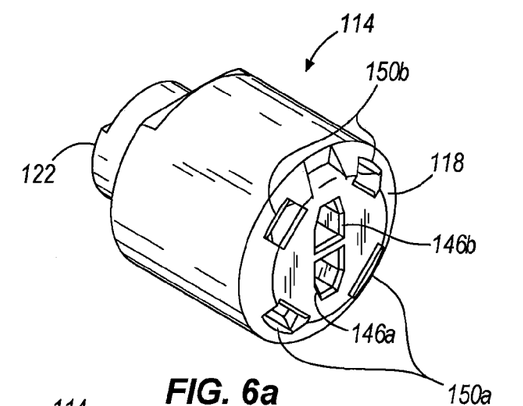
FIG. 6a is a perspective view of an insulation bushing from the insulation bushing assembly of FIG. 3.
Figure 6B:
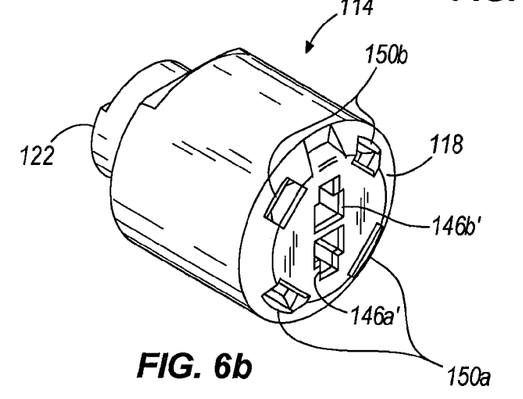
Figure 6C:
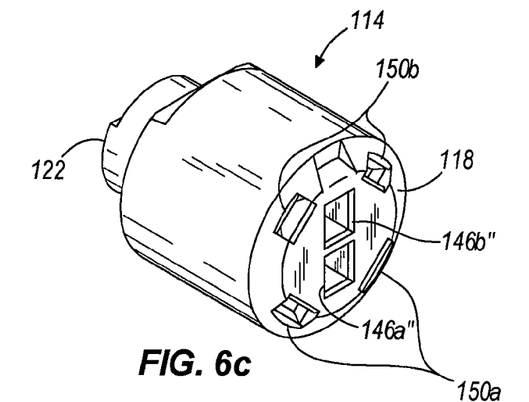

With reference to FIG. 3, an insulation bushing assembly 142 is shown including the insulation bushing 114 and the contact plate assemblies 138a, 138b. Respective openings 146a, 146b to the internal passageways 134a, 134b are shown in the first end 118 of the bushing 114. The openings 146a, 146b define a somewhat tapered shape, however, the openings 146a, 146b may alternatively define other shapes, such as T-shaped openings 146a', 146b' (see FIG. 6b) or square shaped openings 146a", 146b" (see FIG. 6c). The first end 118 of the insulation bushing 114 also includes a first pair of slots 150a spaced from the internal passageway 134a and a second pair of slots 150b spaced from the internal passageway 134b. The purpose of the slots 150a, 150b will be discussed in greater detail below.

Figure 4A:
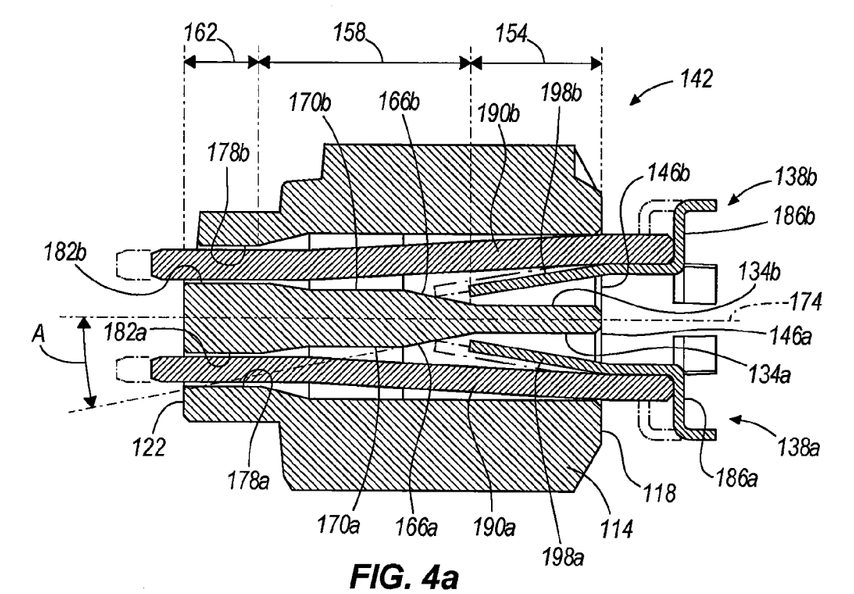

With reference to the internal passageway 134a shown in FIG. 4a (with the same discussion applying to the internal passageway 134b), the passageway 134a may include a first or "entry" portion 154 adjacent the first end 118 of the bushing 114, a second or "transition" portion 158, and a third or "exit" portion 162 adjacent the second end 122 of the bushing 114. As shown in FIG. 4a, the transition portion 158 tapers or narrows the height of the internal passageway 134a from the entry portion 154 to the exit portion 162. More particularly, the transition portion 158 includes a first or "ramp" surface 166a adjacent to a second surface 170a. In the illustrated construction, the second surface 170a is substantially parallel with a longitudinal axis 174 passing through the bushing 114. Also, in the illustrated construction, the ramp surface 166a and the second surface 170a define therebetween an angle A of about 12 degrees. Alternatively, the ramp surface 166a and the second surface 170a may define therebetween an angle A of about 10 degrees to about 12.5 degrees. Further, the internal passageway 134a may be formed differently such that the ramp surface 166a provides a non-linear transition to the second surface 170a. For example, the ramp surface 166a may be defined by a first order curve, a second order curve, an exponential curve, and so forth.

With continued reference to FIG. 4a, the transition portion 158 of the internal passageway 134a may or may not be further tapered or narrowed between the second surface 170a and the second end 122 of the bushing 114. In the illustrated construction, the transition portion 158 is further tapered between the second surface 170a and the second end 122 of the bushing 114. Alternatively, the transition portion 158 may not be tapered axially between the second surface 170a and the second end 122 of the bushing 114.

The exit portion 162 of the internal passageway 134a includes a third surface 178a spaced from the second surface 170a and a fourth surface 182a opposite the third surface 178a. Like the second surface 170a, the third and fourth surfaces 178a, 182a are substantially parallel with the longitudinal axis 174 of the bushing 114.

As shown in FIGS. 1 and 3, each contact plate assembly 138a, 138b includes a contact plate 186a, 186b and a respective contact wire 190a, 190b extending from the contact plate 186a, 186b. In the illustrated construction, the contact wires 190a, 190b are separate components from the contact plates 186a, 186b and are mechanically coupled to the contact plates 186a, 186b. A process such as welding, for example, may be used to mechanically couple the contact wires 190a, 190b with the contact plates 186a, 186b. Alternatively, other processes may be used to mechanically couple the contact wires 190a, 190b with the contact plates 186a, 186b. Further, in alternate constructions, the contact wires 190a, 190b may be integrally formed with the contact plates 186a, 186b.

With reference to the signal contact plate assembly 138a shown in FIG. 1, the contact plate 186a engages the sensor element 46 to electrically contact the reference electrode. Likewise, with reference to the ground contact plate assembly 138b, the contact plate 186b engages the sensor element 46 to electrically contact the exhaust electrode. The contact plates 186a, 186b electrically connect, respectively, with the reference electrode and the exhaust electrode of the sensor element 46 in substantially the same manner as prior art contact plates and prior art sensor elements in prior art sensors. As such, further description of the electrical connection of the contact plates 186a, 186b with the reference and exhaust electrodes, respectively, will be omitted.

With reference to FIG. 3, the contact plate 186a includes a first pair of alignment tabs 194a extending therefrom to engage the first pair of slots 150a in the bushing 114. Likewise, the contact plate 186b includes a second pair of alignment tabs 194b extending therefrom to engage the second pair of slots 150b in the bushing 114. In the illustrated embodiment, the alignment tabs 194a of contact plate 186a are shorter and wider than the alignment tabs 194b of contact plate 186b, and the respective pairs of slots 150a, 150b are appropriately sized to snugly receive the pairs of alignment tabs 194a, 194b. This ensures that the signal and ground contact wires 190a, 190b are inserted into the proper internal passageways 134a, 134b in the bushing 114.

With reference to FIG. 1, the contact plate assemblies 138a, 138b also include resilient members in the form of compression tabs 198a, 198b extending from the respective contact plates 186a, 186b. In the illustrated construction, the compression tabs 198a, 198b are integrally formed with the contact plates 186a, 186b by a process such as, for example, stamping. However, in alternate constructions, the compression tabs 198a, 198b may be separate components that are mechanically coupled to the contact plates 186a, 186b.

Figure 4B:
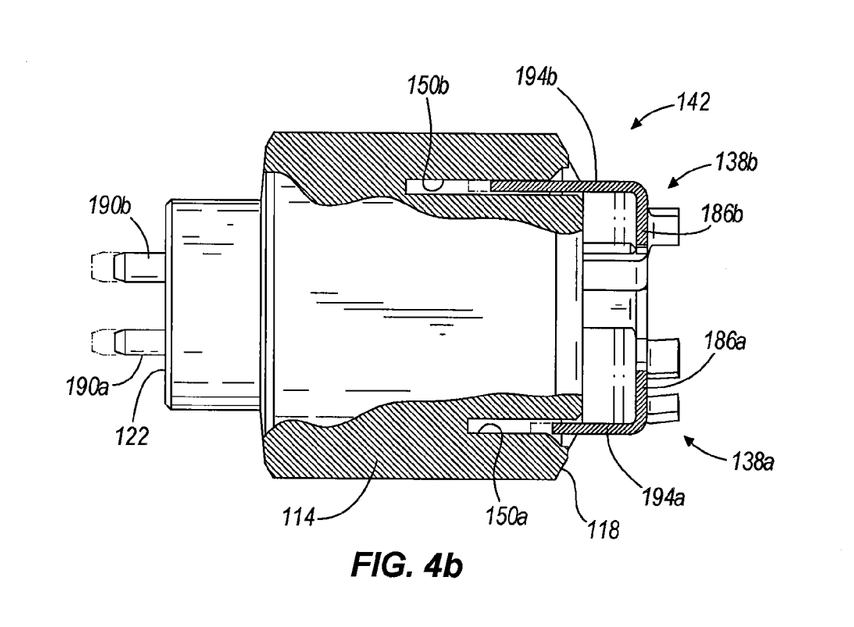
FIG. 4b is a partially assembled, partial cross-sectional view of the insulation bushing assembly of FIG. 3 taken through section line 4b-4b.

During assembly of the insulation bushing assembly 142 (see FIG. 4a), the contact wires 190a, 190b and the compression tabs 198a, 198b are initially inserted into the respective internal passageways 134a, 134b, and the contact plates 186a, 186b are moved toward the first end 118 of the bushing 114. With reference to FIG. 4b, as the contact plates 186a, 186b approach the first end 118 of the bushing 114, the pairs of alignment tabs 194a, 194b of the respective contact plate assemblies 138a, 138b engage the respective pairs of slots 150a, 150b in the first end 118 of the bushing 114 to orient the contact plates 186a, 186b with respect to the bushing 114.

With reference to FIG. 4a, upon continued insertion of the contact wires 190a, 190b and the compression tabs 198a, 198b into the internal passageways 134a, 134b, the resilient compression tabs 198a, 198b deflect upon engaging one or more surfaces in the respective passageways 134a, 134b to develop friction between the one or more surfaces and the compression tabs 198a, 198b and to retain the contact plate assemblies 138a, 138b in the respective internal passageways 134a, 134b.

More particularly, with exemplary reference to the compression tab 198a (with the same discussion applying to the compression tab 198b and the internal passageway 134b), the compression tab 198a assumes an undeflected position upon initial insertion into the entry portion 154 of the internal passageway 134a. With continued insertion into the internal passageway 134a, the compression tab 198a encounters the ramp surface 166a in the passageway 134a that causes the compression tab 198a to deflect toward the contact wire 190a. The ramp surface 166a, in other words, causes the compression tab 198a to move from an initial undeflected position to a deflected position upon continued insertion into the passageway 134a.

Since the compression tab 198a is resilient, the tab 198a applies a force to the ramp surface 166a as it is deflected. The ramp surface 166a therefore applies a reaction force, or a normal force, to the compression tab 198a to balance the force applied by the compression tab 198a. Such a normal force includes a component that is transverse to the longitudinal axis 174, which results in a frictional force developed between the compression tab 198a and the ramp surface 166a, and a component that is parallel to the longitudinal axis 174, which tends to urge the contact plate 186a away from the first end 118 of the bushing 114.

For the compression tab 198a to deflect upon engaging the ramp surface 166a, the contact plate 186a should be maintained in a substantially fixed orientation with respect to the insulation bushing 114 (i.e., the contact plate 186a should be kept substantially parallel with the first end 118 of the insulation bushing 114) during insertion of the contact plate assembly 138a into the internal passageway 134a. As shown in FIG. 4b, the pair of alignment tabs 194a of the contact plate assembly 138a engage the respective pair of slots 150a in the first end 118 of the bushing 114 before the compression tab 198 encounters or engages the ramp surface 166a. As a result, the pair of alignment tabs 194a maintain the contact plate 186a in a substantially fixed orientation when the compression tab 198a engages the ramp surface 166a. The pair of alignment tabs 194a therefore facilitates an automated assembly process of inserting the contact plate assembly 138a into the insulation bushing 114.

Figure 5A:
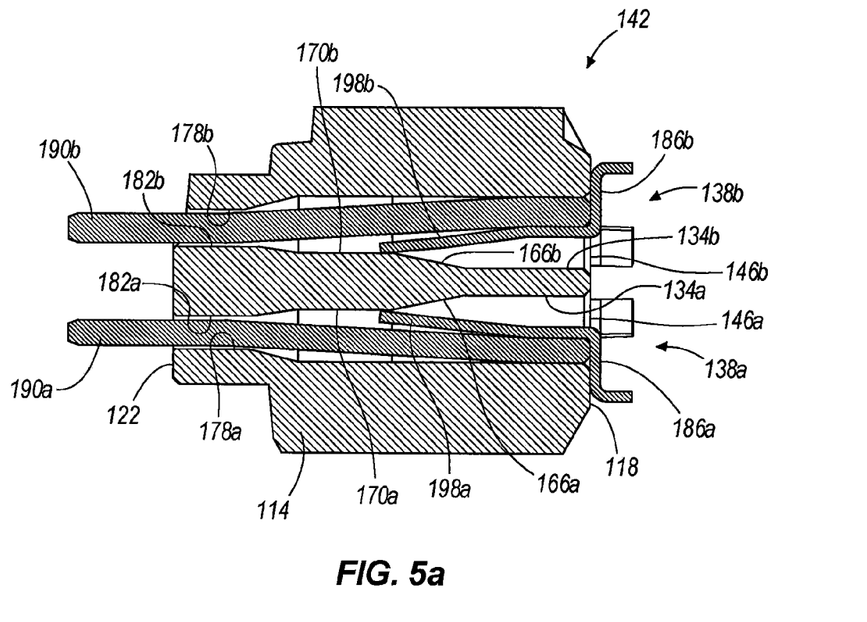
Figure 5B:
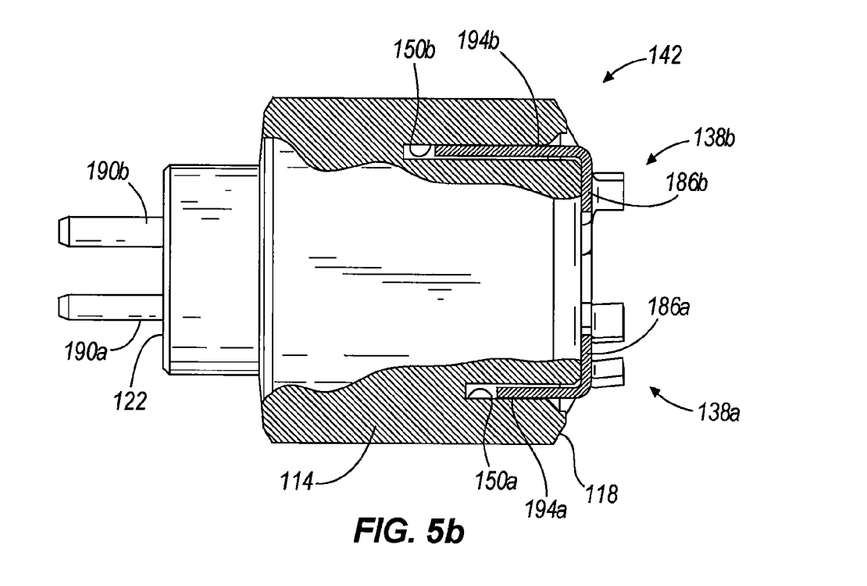
FIG. 5b is an assembled, partial cross-sectional view of the insulation bushing assembly of FIG. 3 taken through section line 5b-5b.

With reference to FIG. 5a, the compression tab 198a encounters the second surface 170a after traversing the ramp surface 166a during continued insertion into the internal passageway 134a. Upon engaging the second surface 170a, the compression tab 198a is maintained in a deflected position. FIG. 5a shows the contact plate assembly 138a fully engaged with the internal passageway 134a, and the compression tab 198a maintained in a deflected position by the second surface 170a of the internal passageway 134a. Since the compression tab 198a is resilient, the tab 198a applies a force to the second surface 170a, which, in turn, applies a reaction force or a normal force to the compression tab 198a to balance the force applied by the compression tab 198a. Unlike the ramp surface 166a, the normal force is applied to the compression tab 198a entirely in a direction transverse to the longitudinal axis 174 (i.e., a component of the normal force that would urge the contact plate 186a away from the first surface 118 of the bushing 114 does not exist when the compression tab 198a is engaging the second surface 170a).

Such a normal force allows a frictional force to develop between the compression tab 198a and the second surface 170a. The frictional force is sufficient to maintain the contact plate assembly 138a engaged with the internal passageway 134a when, for example, the bushing 114 is oriented substantially vertically with the engaged contact plate 186a at the lower end. Even in this orientation, the weight of the contact plate assembly 138a by itself is not sufficient to cause the contact plate assembly 138a to fall out of the internal passageway 134a. This facilitates handling, manipulation, and further assembly of the assembled bushing 114 and contact plate assemblies 138a, 138b.

Alternatively, locking structure (e.g., a detent configuration) may be incorporated on one or more of the internal passageways 134a, 134b and the compression tabs 198a, 198b, such that the contact plate assemblies 138a, 138b may be retained in the bushing 114. However, such locking structure may not result in the contact plate assemblies 138a, 138b being releasable from the bushing 114 if later desired.

With continued reference to FIG. 5a (with the same discussion applying to the contact wire 190b and the internal passageway 134b), the contact wire 190a is not engaged with any surface in the exit portion 162 of the internal passageway 134a. More particularly, the contact wire 190a is spaced from the third and fourth surfaces 178a, 182a of the internal passageway 134a, such that the contact wire 190a does not frictionally engage either of the third or fourth surfaces 178a, 182a.

Figure 7:
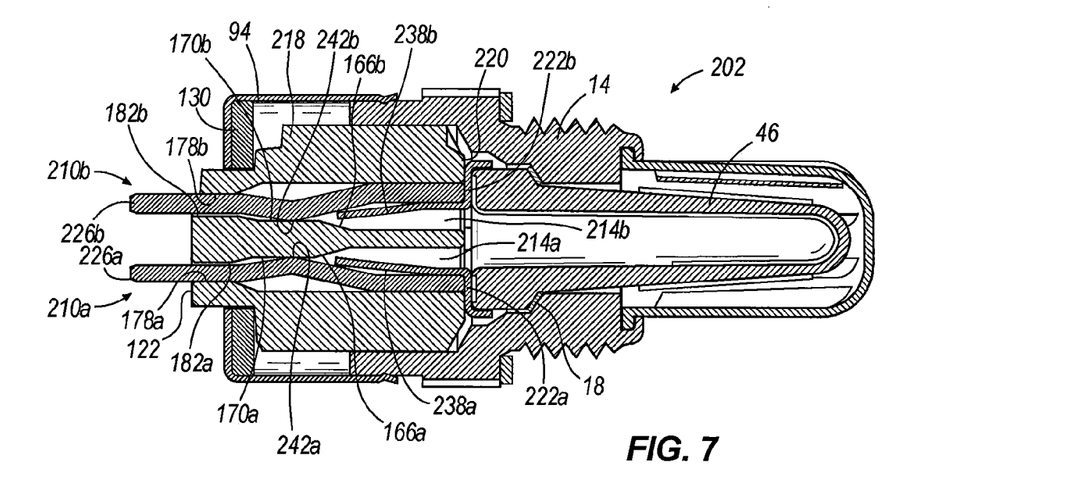
FIG. 7 is a cross-sectional view of another construction of an exhaust gas sensor of the present invention.

FIG. 7 illustrates another exhaust gas sensor 202 of the present invention utilizing another configuration of an insulation bushing assembly 206. With the exception of the insulation bushing assembly 206, the remaining components of the sensor 202 of FIG. 7 are substantially similar to those discussed above with reference to the sensor 10 of FIG. 1. As such, like components will be labeled with like reference numerals.

Figure 8:
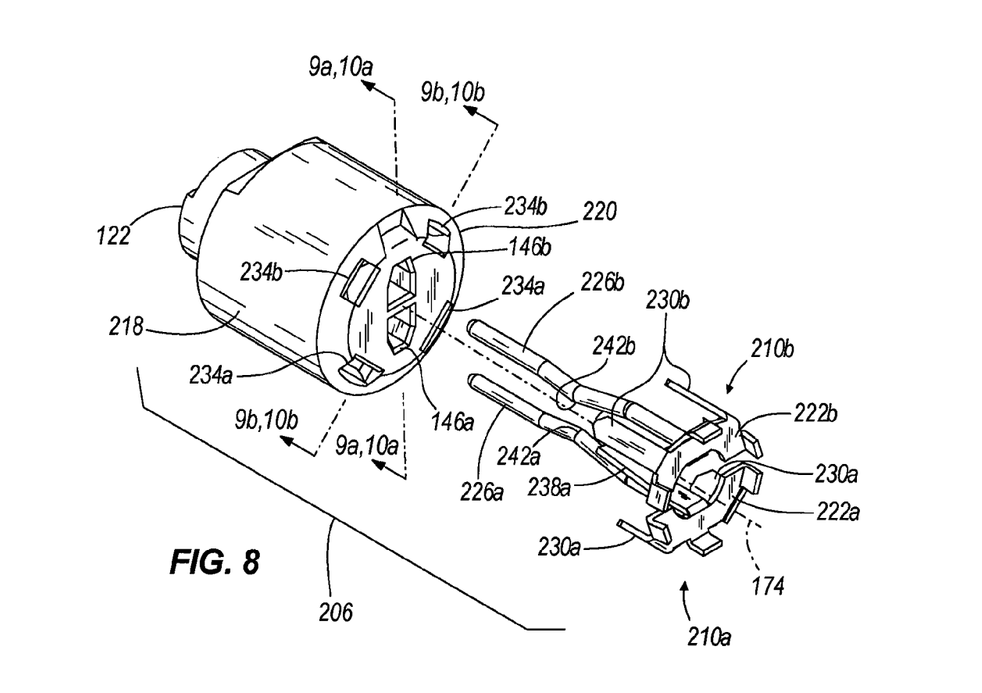
FIG. 8 is an enlarged, exploded, perspective view of an insulation bushing assembly from the sensor of FIG. 7.

With reference to FIGS. 7 and 8, the insulation bushing assembly 206 includes a "signal" contact plate assembly 210a and a "ground" contact plate assembly 210b engageable with respective internal passageways 214a, 214b in an insulation bushing 218. The insulation bushing 218 is substantially similar to the insulation bushing 114 of the sensor 10 of FIG. 1, however, the transition portion 158 of the insulation bushing 218 is positioned further from a first end 220 of the bushing 218 compared to the transition portion 158 of the bushing 114 of the sensor 10 of FIG. 1. As such, the ramp surfaces 166a, 166b, the second surfaces 170a, 170b, the third surfaces 178a, 178b, and the fourth surfaces 182a, 182b of the internal passageways 214a, 214b will be labeled with like reference numerals as the same surfaces of the bushing 114 of the sensor 10 of FIG. 1.

The contact plate assemblies 210a, 210b include respective contact plates 222a, 222b and respective contact wires 226a, 226b mechanically coupled to the contact plates 222a, 222b in a similar fashion as the contact wires 190a, 190b and the contact plates 186a, 186b of the sensor 10 of FIG. 1. Except as described below, the contact plates 222a, 222b are substantially similar to the contact plates 186a, 186b of the sensor 10 of FIG. 1, and include respective pairs of alignment tabs 230a, 230b that are engageable with respective pairs of slots 234a, 234b in the first end 220 of the insulation bushing 218 to ensure that the signal and ground contact wires 226a, 226b are inserted into the proper internal passageways 214a, 214b in the bushing 218. The contact plates 222a, 222b also include respective compression tabs 238a, 238b integrally formed with the contact plates 222a, 222b.

However, the contact wires 226a, 226b have a different configuration than the contact wires 190a, 190b of the sensor 10 of FIG. 1. The contact wires 226a, 226b, as shown in FIGS. 7 and 8, include respective raised portions or apices 242a, 242b as the result of multiple bends formed in the contact wires 226a, 226b or multiple curves formed in the contact wires 226a, 226b. As will be described below, in this embodiment the contact wires 226a, 226b act as resilient members to help retain the contact plate assemblies 210a, 210b engaged with the bushing 218.

Figure 9A:
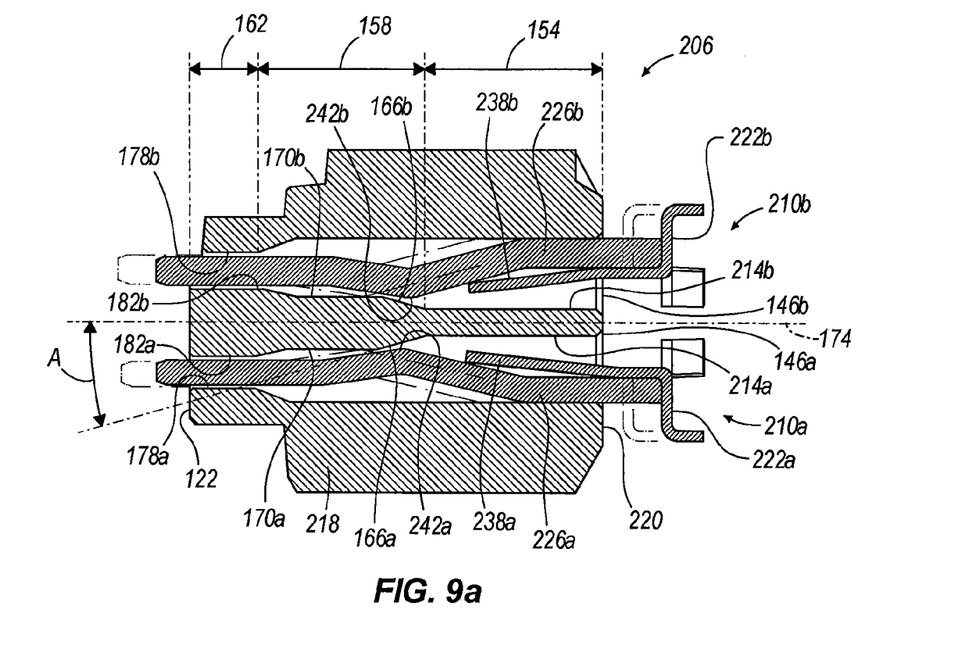
Figure 9B:
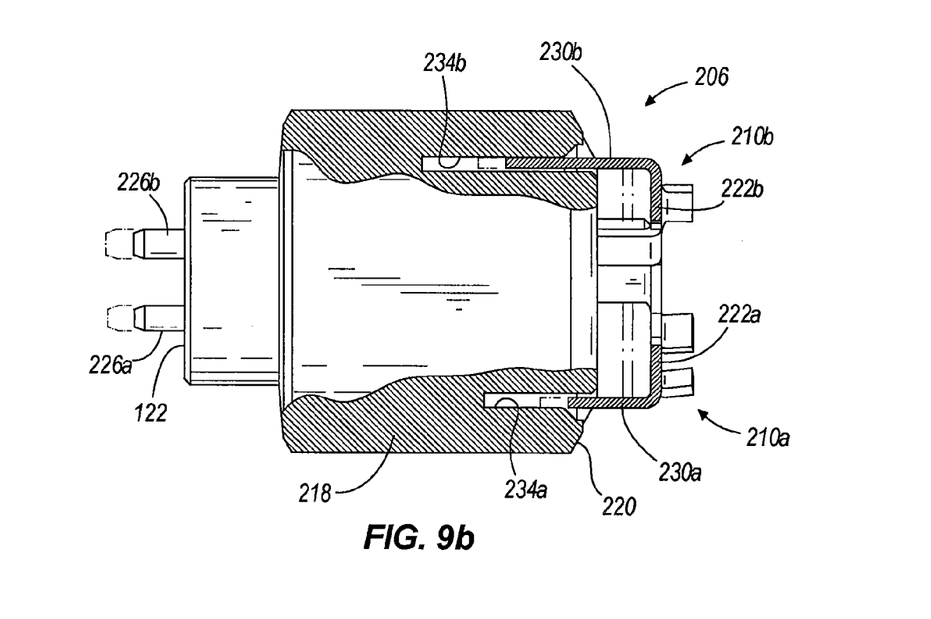
FIG. 9b is a partially assembled, partial cross-sectional view of the insulation bushing assembly of FIG. 8 taken through section line 9b-9b.

With reference to FIG. 9a, the contact wires 226a, 226b, upon insertion into the respective internal passageways 214a, 214b, deflect upon engaging one or more surfaces in the passageways 214a, 214b to develop friction between the one or more surfaces and the contact wires 226a, 226b. As such, the contact wires 226a, 226b act as the resilient members rather than, or possibly in addition to, the compression tabs 238a, 238b. The compression tabs 238a, 238b, as shown in FIG. 10a, do not engage any surface in the internal passageways 214a, 214b and therefore, in alternate constructions of the contact plate assemblies 210a, 210b, may be eliminated.

More particularly, with exemplary reference to the contact wire 226a (with the same discussion applying to the contact wire 226b and the internal passageway 214b), the contact wire 226a assumes an undeflected position upon initial insertion into the entry portion 154 of the internal passageway 214a (see FIG. 9a). With continued insertion into the internal passageway 214a, the contact wire 226a, and more particularly the apex 242a of the contact wire 226a, encounters the ramp surface 166a to cause the contact wire 226a to deflect radially outwardly to a deflected position.

Since the contact wire 226a is resilient, the wire 226a applies a force to the ramp surface 166a as it is deflected. The ramp surface 166a therefore applies a reaction force, or a normal force, to the contact wire 226a to balance the force applied by the contact wire 226a. Such a normal force includes a component that is transverse to the longitudinal axis 174, which results in a frictional force developed between the contact wire 226a and the ramp surface 166a, and a component that is parallel to the longitudinal axis 174, which tends to urge the contact plate 222a away from the first end 220 of the bushing 218.

Figure 10A:
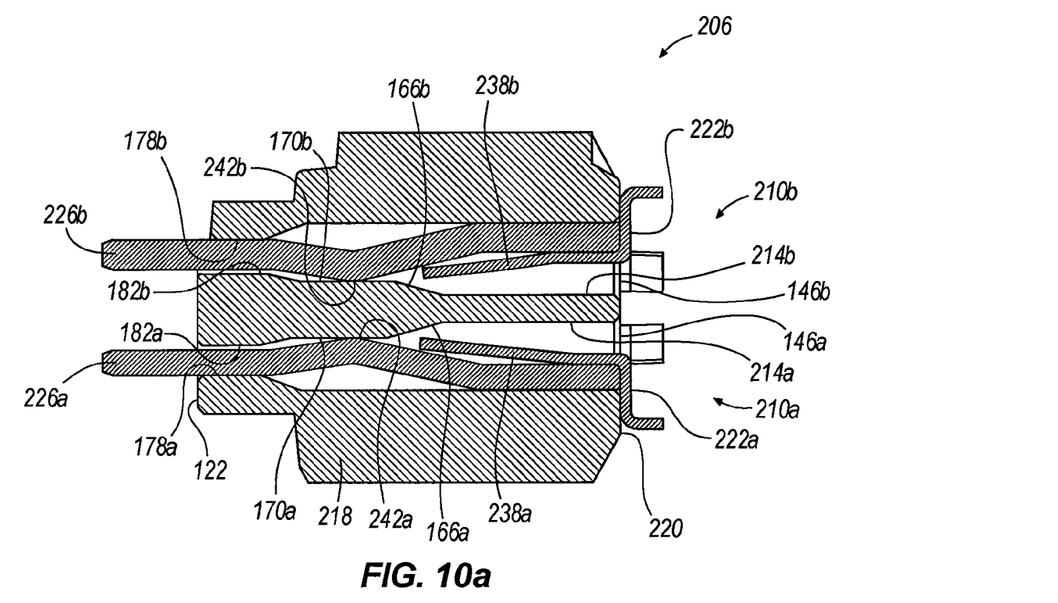
Figure 10B:
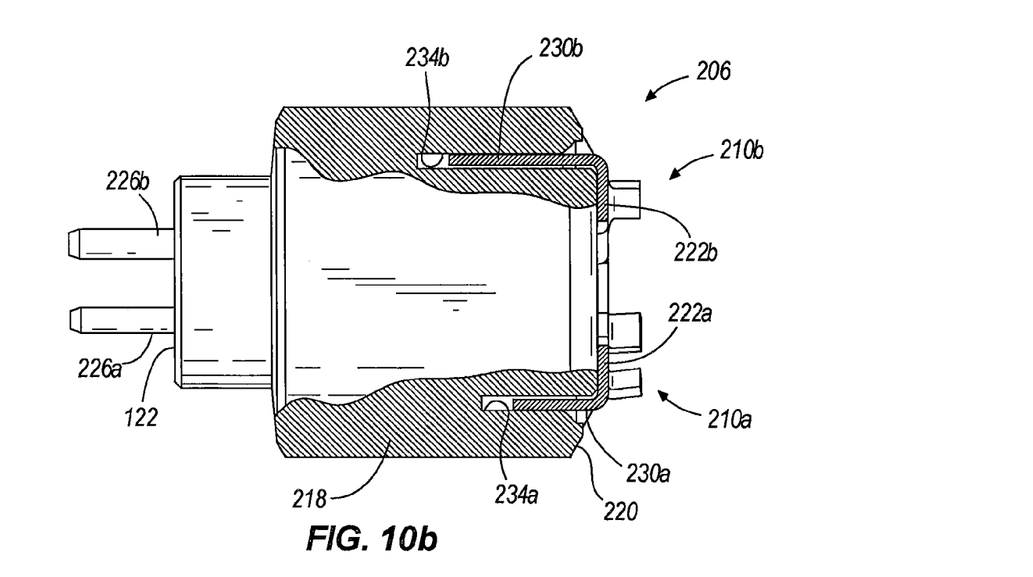
FIG. 10b is an assembled, partial cross-sectional view of the insulation bushing assembly of FIG. 8 taken through section line 10b-10b.

With reference to FIG. 10a, the apex 242a of the contact wire 226a encounters the second surface 170a after traversing the ramp surface 166a during continued insertion into the internal passageway 214a. Upon engaging the second surface 170a, the contact wire 226a is maintained in a deflected position by the frictional force between the apex 242a of the contact wire 226a and the second surface 170a, similar to the frictional engagement of the compression tab 198a and the second surface 170a of the sensor 10 of FIG. 1.

Such a frictional force is sufficient to maintain the contact plate assembly 210a engaged with the internal passageway 214a when, for example, the bushing 218 is oriented substantially vertically with the engaged contact plate 222a at the lower end. Even in this orientation, the weight of the contact plate assembly 210a by itself is not sufficient to cause the contact plate assembly 210a to fall out of the internal passageway 214a. This facilitates handling, manipulation, and further assembly of the assembled bushing 218 and contact plate assemblies 210a, 210b.

With continued reference to FIG. 10a (with the same discussion applying to the contact wire 226b and the internal passageway 214b), deflection of the contact wire 226a also causes the contact wire 226a to engage the third surface 178a in the exit portion 162a of the internal passageway 214a. In the illustrated construction, the contact wire 226a is also spaced from the fourth surface 182a in the exit portion 162a of the internal passageway 214a. However, the contact wire 226a may alternatively engage both of the third and fourth surfaces 178a, 182a. The frictional forces developed between the contact wire 226a and the third surface 178a, in addition to the frictional forces developed between the contact wire 226a and the second surface 170a, help prevent unintentional disengagement of the contact plate assembly 210a from the internal passageway 214a.

Figure 11:
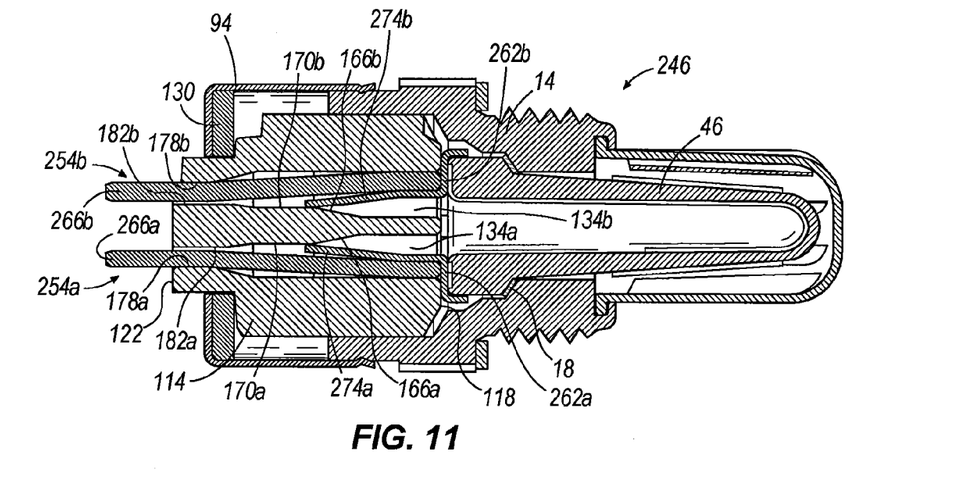
FIG. 11 is a cross-sectional view of yet another construction of an exhaust gas sensor of the present invention.

FIG. 11 illustrates yet another exhaust gas sensor 246 of the present invention utilizing yet another configuration of an insulation bushing assembly 250. The insulation bushing assembly 250 includes a "signal" contact plate assembly 254a and a "ground" contact plate assembly 254b engageable with respective internal passageways 134a, 134b in the insulation bushing 114. With the exception of the contact plate assemblies 254a, 254b, the remaining components of the sensor 246 of FIG. 11 are substantially similar to those discussed above with reference to the sensor 10 of FIG. 1. As such, like components will be labeled with like reference numerals.

The contact plate assemblies 254a, 254b include respective contact plates 262a, 262b and respective contact wires 266a, 266b mechanically coupled to the contact plates 262a, 262b in a similar fashion as the contact wires 190a, 190b and the contact plates 186a, 186b of the sensor 10 of FIG. 1. The contact plates 262a, 262b include respective pairs of alignment tabs 270a, 270b that are engageable with respective pairs of slots 150a,b150b in the first end 118 of the insulation bushing 114 to ensure that the signal and ground contact wires 266a, 266b are inserted into the proper internal passageways 134a, 134b in the bushing 114. The contact plates 262a, 262b also include respective compression tabs 274a, 274b integrally formed with the contact plates 262a, 262b.

However, the contact wires 266a, 266b have a different configuration than the contact wires 190a, 190b of the sensor 10 of FIG. 1. More particularly, with reference to the contact wire 266a (with the same discussion applying to the contact wire 266b and the internal passageway 134b), the contact wire 266a is bent or curved to at least partially engage the third surface 178a in the exit portion 162 of the internal passageway 134a, as discussed below.

Figure 13A:
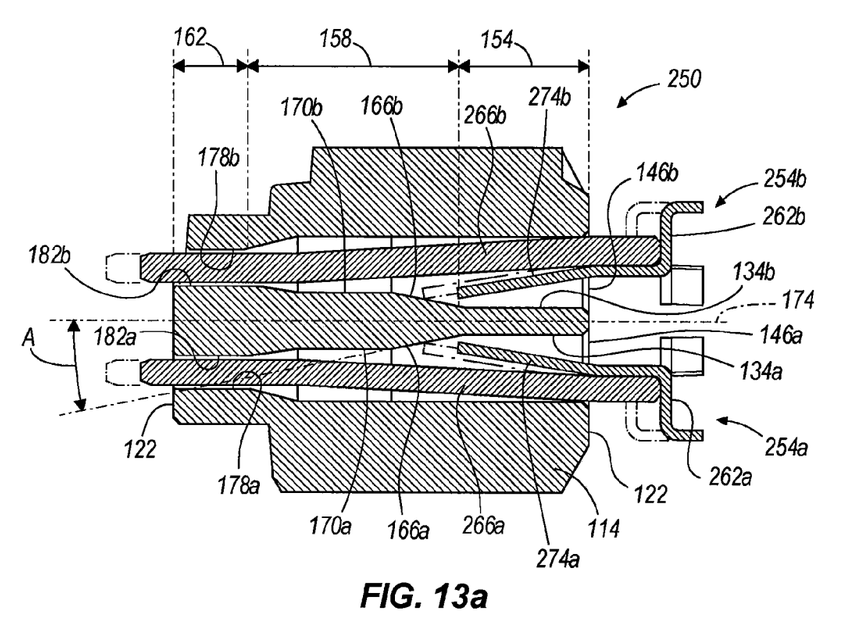
Figure 13B:
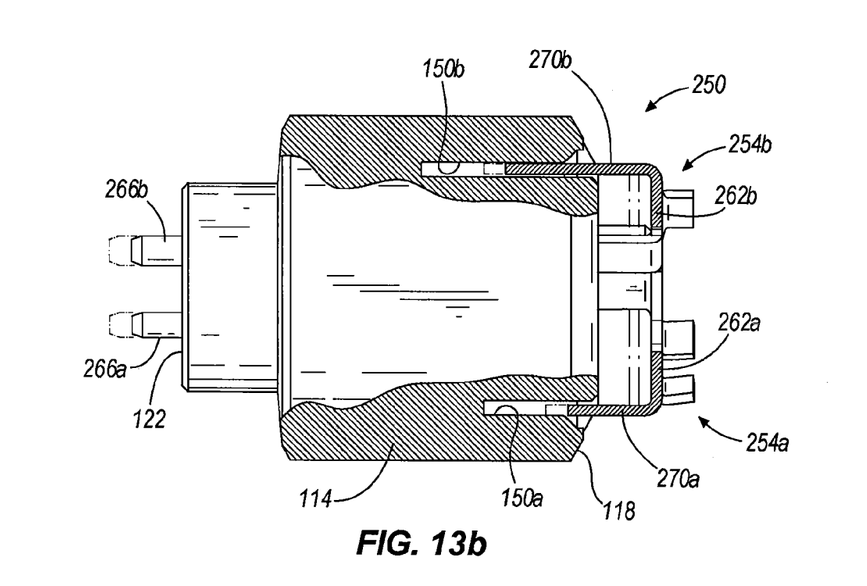
FIG. 13b is a partially assembled, partial cross-sectional view of the insulation bushing assembly of FIG. 12 taken through section line 13b-13b.

With reference to FIG. 13a, the compression tabs 274a, 274b, upon insertion into the respective internal passageways 134a, 134b, deflect upon engaging one or more surfaces in the passageways 134a, 134b to develop friction between the one or more surfaces and the compression tabs 274a, 274b. As such, the compression tabs 274a, 274b act as resilient members to help retain the contact plate assemblies 254a, 254b engaged with the bushing 114.

More particularly, with exemplary reference to the compression tab 274a (with the same discussion applying to the compression tab 274b and the internal passageway 134b), the compression tab 274a assumes an undeflected position upon initial insertion into the entry portion 154 of the internal passageway 134a. With continued insertion into the internal passageway 134a, the compression tab 274a encounters the ramp surface 166a to cause the compression tab 274a to deflect radially outwardly to a deflected position.

Figure 14A:
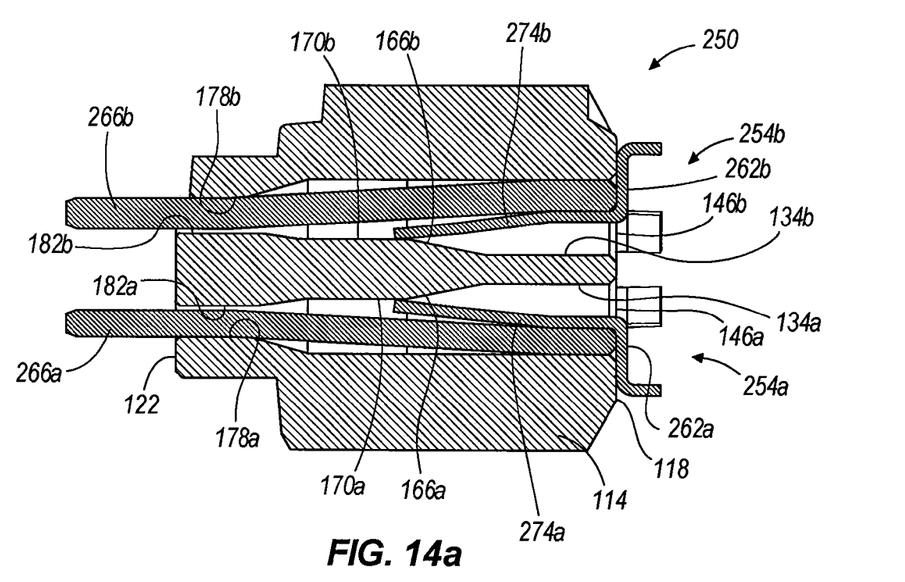
Figure 14B:
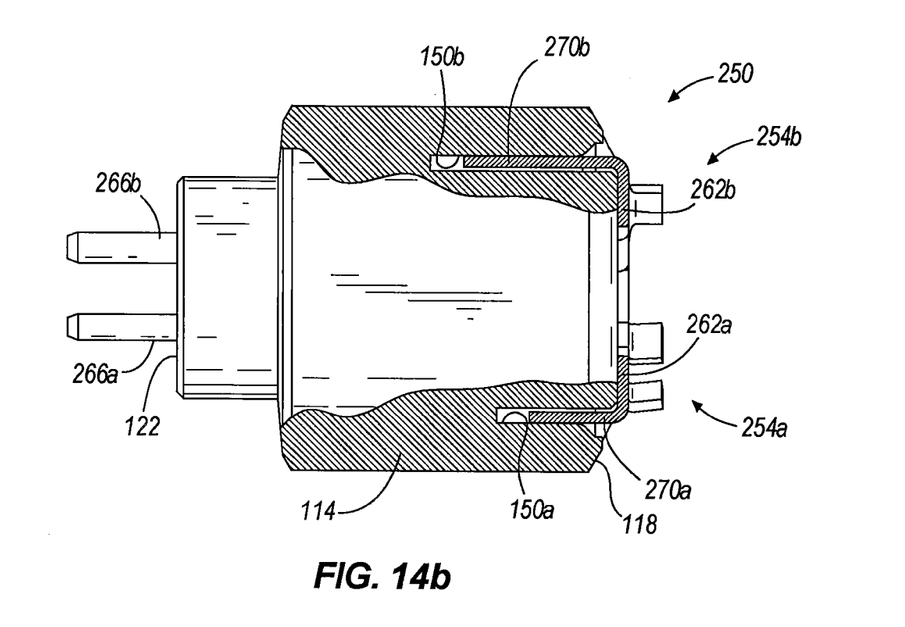
FIG. 14b is an assembled, partial cross-sectional view of the insulation bushing assembly of FIG. 12 taken through section line 14b-14b.

With reference to FIG. 14a, the compression tab 274a encounters the second surface 170a after traversing the ramp surface 166a during continued insertion into the internal passageway 134a. Upon engaging the second surface 170a, the compression tab 274a is maintained in a deflected position by the frictional force between the compression tab 274a and the second surface 170a, similar to the frictional engagement of the compression tab 198a and the second surface 170a of the sensor 10 of FIG. 1.

Such a frictional force is sufficient to maintain the contact plate assembly 254a engaged with the internal passageway 134a when, for example, the bushing 114 is oriented substantially vertically with the engaged contact plate 262a at the lower end. Even in this orientation, the weight of the contact plate assembly 254a by itself is not sufficient to cause the contact plate assembly 254a to fall out of the internal passageway 134a. This facilitates handling, manipulation, and further assembly of the assembled bushing 114 and contact plate assembly 254a.

With continued reference to FIG. 10a, the contact wire 266a may be at least partially deflected such that at least a portion of the contact wire 266a engages the third surface 178a in the exit portion 162 of the internal passageway 134a. As such, the contact wire 266a may also act as a resilient member to help retain the contact plate assembly 254a engaged with the bushing 114. In the illustrated construction, the contact wire 266a is also spaced from the fourth surface 182a in the exit portion 162 of the internal passageway 134a. However, the contact wire 266a may alternatively engage both of the third and fourth surfaces 178a, 182a. The frictional forces developed between the contact wire 266a and the third surface 178a, in addition to the frictional forces developed between the compression tab 274a and the second surface 170a, help prevent unintentional disengagement of the contact plate assembly 254a from the internal passageway 134a.

Figure 12:
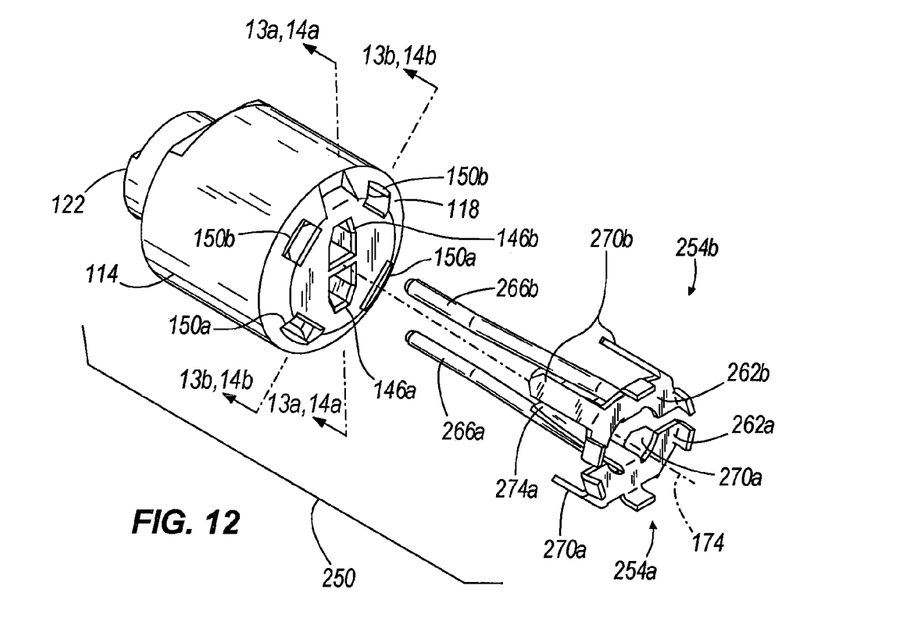
FIG. 12 is an enlarged, exploded, perspective view of an insulation bushing assembly from the sensor of FIG. 11.

The insulation bushing assemblies 142, 206, 250 of FIGS. 3, 8, and 12 provide an improved method of assembling the respective sensors 10, 202, 246 of FIGS. 1, 7, and 11. More particularly, the insulation bushing assemblies 142, 206, 250 may be inverted or positioned in a substantially vertical orientation at any time during the assembly process while substantially preventing the contact plate assemblies 138a, 138b, 210a, 210b, 254a, 254b from falling out of the bushing 114 or 218. This enables a more streamlined and efficient assembly process compared to processes that must accommodate prior art contact plate assemblies, which are not frictionally maintained in the insulation bushings immediately after insertion. Such prior art contact plate assemblies and prior art insulation bushings typically require a more complex and less efficient assembly process since their design inherently places constraints (e.g., not being able to be inverted) on the assembly process.

Various features of the invention are set forth in the following claims.

We claim:

1. An insulation bushing assembly for use with an exhaust gas sensor, the insulation bushing assembly comprising:
   an insulation bushing including a passageway defining a surface; and
   a contact plate assembly having
      a contact plate coupled with the insulation bushing, the contact plate having a substantially planar surface engageable with one of an exhaust electrode and a reference electrode in the exhaust gas sensor; and
      a resilient member extending from the contact plate for insertion into the passageway, the resilient member engageable with the surface of the passageway during insertion such that the member is deflected by the surface from an undeflected position with respect to the contact plate to a deflected position with respect to the contact plate.

2. The assembly of claim 1, wherein the surface is a first surface, and wherein the passageway further defines a second surface adjacent the first surface, the resilient member engageable with the second surface upon continued insertion to maintain the member in the deflected position to retain the contact plate assembly in engagement with the bushing.

3. The assembly of claim 2, wherein the first and second surfaces define an oblique angle therebetween.

4. The assembly of claim 2, wherein the first surface and the second surface define an angle therebetween of about 10 to about 12.5 degrees.

5. The assembly of claim 1, further comprising a contact wire extending from the contact plate for insertion into the passageway, wherein the resilient member comprises a compression tab separate from the contact wire.

6. The assembly of claim 1, wherein the resilient member comprises a contact wire.

7. The assembly of claim 6, wherein the contact wire defines an apex engageable with the surface of the passageway.

8. The assembly of claim 6, wherein the surface is a first surface, and wherein the contact wire is engageable with at least one additional surface of the passageway spaced from the first surface.

9. The assembly of claim 1, wherein the resilient member comprises at least one of a contact wire and a compression tab.

10. The assembly of claim 9, wherein the surface is a first surface, wherein the compression tab is engageable with the first surface of the passageway, and wherein the contact wire is engageable with at least one additional surface of the passageway spaced from the first surface.

11. The assembly of claim 1, wherein the insulation bushing further includes a slot spaced from the passageway, and wherein the contact plate assembly further includes an alignment tab extending from the contact plate and engageable with the slot to orient the contact plate with respect to the insulation bushing.

12. The assembly of claim 11, wherein the alignment tab is at least partially engaged with the slot before the resilient member is deflected to its deflected position by the surface of the passageway.

13. An exhaust gas sensor comprising:
a sensor housing;
a sensor element at least partially enclosed within the housing, the sensor element including at least one of an exhaust electrode and a reference electrode;
an insulation bushing at least partially supported within the housing, the insulation bushing including a passageway defining a surface; and
a contact plate assembly having
a contact plate coupled with the insulation bushing and having a substantially planar surface engaged with one of the exhaust electrode and the reference electrode; and
a resilient member extending from the contact plate for insertion into the passageway, the resilient member engageable with the surface of the passageway during insertion such that the member is deflected by the surface from an undeflected position with respect to the contact plate to a deflected position with respect to the contact plate.

14. The assembly of claim 13, wherein the surface is a first surface, and wherein the passageway further defines a second surface adjacent the first surface, the resilient member engageable with the second surface upon continued insertion to maintain the member in the deflected position to retain the contact plate assembly in engagement with the bushing.

15. The assembly of claim 14, wherein the first and second surfaces define an oblique angle therebetween.

16. The assembly of claim 14, wherein the first surface and the second surface define an angle therebetween of about 10 to about 12.5 degrees.

17. The assembly of claim 13, further comprising a contact wire extending from the contact plate for insertion into the passageway, wherein the resilient member comprises a compression tab separate from the contact wire.

18. The assembly of claim 13, wherein the resilient member comprises a contact wire.

19. The assembly of claim 18, wherein the contact wire defines an apex engageable with the surface of the passageway.

20. The assembly of claim 18, wherein the surface is a first surface, and wherein the contact wire is engageable with at least one additional surface of the passageway spaced from the first surface.

21. The assembly of claim 13, wherein the resilient member comprises at least one of a contact wire and a compression tab.

22. The assembly of claim 21, wherein the surface is a first surface, wherein the compression tab is engageable with the first surface of the passageway, and wherein the contact wire is engageable with at least one additional surface of the passageway spaced from the first surface.

23. The assembly of claim 13, wherein the insulation bushing further includes a slot spaced from the passageway, and wherein the contact plate assembly further includes an alignment tab extending from the contact plate and engageable with the slot to orient the contact plate with respect to the insulation bushing.

24. The assembly of claim 23, wherein the alignment tab is at least partially engaged with the slot before the resilient member is deflected to its deflected position by the surface of the passageway.

25. A method of assembling an exhaust gas sensor, the method comprising:
providing an insulation bushing including a passageway defining a surface;
providing a contact plate assembly including a contact plate and a resilient member extending from the contact plate;
inserting the resilient member into the passageway;
engaging the resilient member with the surface;
deflecting the resilient member from an undeflected position with respect to the contact plate to a deflected position with respect to the contact plate; and
engaging a substantially planar surface of the contact plate with one of an exhaust electrode and a reference electrode of the exhaust gas sensor.

26. The method of claim 25, wherein the surface is a first surface, and wherein the method further includes engaging the resilient member with a second surface adjacent the first surface to maintain the resilient member in the deflected position to retain the contact plate assembly in engagement with the bushing.

27. The method of claim 25, wherein the contact plate assembly includes a contact wire and a compression tab extending from the contact plate, and wherein engaging the resilient member with the surface includes engaging the compression tab with the surface.

28. The method of claim 25, wherein the contact plate assembly includes a contact wire extending from the contact plate, and wherein engaging the resilient member with the surface includes engaging the contact wire with the surface.

29. The method of claim 25, wherein the contact plate assembly includes a contact wire and a compression tab extending from the contact plate, wherein the surface is a first surface, wherein engaging the resilient member with the first surface includes engaging the compression tab with the first surface, and wherein the method further includes engaging the contact wire with at least one additional surface of the passageway spaced from the first surface.

30. The method of claim 25, wherein the contact plate assembly includes an alignment tab extending from the contact plate, and wherein the method further includes engaging the alignment tab with a slot in the insulation bushing to orient the contact plate with respect to the insulation bushing.

31. The method of claim 30, further comprising at least partially engaging the alignment tab with the slot before engaging the resilient member with the surface.

* * * * *